(12) United States Patent
Hwang

(10) Patent No.: US 8,351,655 B2
(45) Date of Patent: Jan. 8, 2013

(54) METHOD AND SYSTEM FOR AUTOMATICALLY GRADING BEEF QUALITY

(75) Inventor: Heon Hwang, Seoul (KR)

(73) Assignee: Sungkyunkwan University Foundation for Corporate Collaboration, Gyeonggi-Do (KR)

(*) Notice: Subject to any disclaimer, the term of this patent is extended or adjusted under 35 U.S.C. 154(b) by 440 days.

(21) Appl. No.: 12/657,648

(22) Filed: Jan. 25, 2010

(65) Prior Publication Data

US 2011/0110563 A1 May 12, 2011

(30) Foreign Application Priority Data

Jul. 29, 2009 (KR) .................. 10-2009-0069662

(51) Int. Cl.
*G06K 9/00* (2006.01)
(52) U.S. Cl. .................. 382/110; 348/135; 345/611
(58) Field of Classification Search .................. 382/100, 382/103, 110, 141, 254–266, 275, 199, 200; 345/611; 348/92, 135, 143
See application file for complete search history.

(56) References Cited

U.S. PATENT DOCUMENTS

| 5,339,815 | A | * | 8/1994 | Liu et al. ................. 600/437 |
| 5,793,879 | A | * | 8/1998 | Benn et al. ................. 382/110 |
| 5,944,598 | A | * | 8/1999 | Tong et al. ................. 452/158 |
| 5,960,105 | A | * | 9/1999 | Brethour ................. 382/141 |
| 6,751,364 | B2 | * | 6/2004 | Haagensen et al. ......... 382/313 |
| 6,891,961 | B2 | * | 5/2005 | Eger et al. ................. 382/110 |
| 2004/0125987 | A1 | * | 7/2004 | Haagensen et al. ......... 382/110 |

* cited by examiner

*Primary Examiner* — Anand Bhatnagar
(74) *Attorney, Agent, or Firm* — Renner, Otto, Boisselle & Sklar, LLP

(57) ABSTRACT

A method of automatically grading beef quality by analyzing a digital image is provided. The method includes: an image acquiring step of acquiring a color image of beef using a CCD camera; a region separating step of separating a lean region from the acquired image; a boundary extracting step of extracting a boundary line of the lean region; a boundary smoothing step of smoothing the boundary line extracted in the boundary extracting step; a boundary correcting step of correcting an indented portion and a protruded portion included in the boundary line having been subjected to the boundary smoothing step; a grading region determining step of determining a grading region on the basis of the boundary line corrected in the boundary correcting step; and a grading step of grading the beef quality on the basis of the image of the grading region.

17 Claims, 14 Drawing Sheets
(9 of 14 Drawing Sheet(s) Filed in Color)

METHOD AND SYSTEM FOR AUTOMATICALLY GRADING BEEF QUALITY

This application claims priority of Korean Patent Application No. 10-2009-0069662 filed Jul. 29, 2009, which is hereby incorporated herein by reference in its entirety.

BACKGROUND

1. Field of the Invention

The present invention relates to a method and a system for grading beef quality, and more particularly, to a method and a system for automatically grading beef quality by analyzing a digital image.

2. Description of the Related Art

In general, beef quality is graded just after butchering and the price of beef is determined depending on the grade. The grades of beef quality are determined on the basis of grades of meat quality and quantity and the grading is made with a specialized grader's naked eye.

However, the grading with the naked eye has a problem in that the objectivity of the grading result is not guaranteed because it is difficult to accumulate data quantized by grading items. There are problems in that time of the grading is very long and it is difficult to train specialized graders because of the importance in experience.

Techniques for automatically grading beef quality by image analysis have been studied to solve the above-mentioned problems and have attracted attentions more and more with improvement in digital imaging techniques. However, since lean and fat are mixed in a section of beef and are not clearly distinguished from each other, boundary lines of grading regions extracted in the related art are greatly different from boundary lines extracted by specialized graders.

Therefore, in the automatic grading, it is very important to invent a new method of extracting grading regions with boundary lines similar to the boundary lines extracted by the specialized graders.

SUMMARY

An advantage of some aspects of the invention is that it provides a method and a system for automatically grading beef quality by image analysis after determining a grading region with a boundary line substantially similar to a boundary line extracted by a specialized grader.

According to an aspect of the invention, there is provided a method of automatically grading beef quality, including: an image acquiring step of acquiring a color image of beef using a CCD camera; a region separating step of separating a lean region from the acquired image; a boundary extracting step of extracting a boundary line of the lean region; a boundary smoothing step of smoothing the boundary line extracted in the boundary extracting step; a boundary correcting step of correcting an indented portion and a protruded portion included in the boundary line having been subjected to the boundary smoothing step; a grading region determining step of determining a grading region on the basis of the boundary line corrected in the boundary correcting step; and a grading step of grading the beef quality on the basis of the image of the grading region.

The boundary smoothing step may employ a curve generating method using relationships of pixels selected from pixels in the boundary line. Here, the pixels in a part with a complex boundary line may be selected so that a distance between the pixels is small, and the pixels in a part with a smooth boundary line may be selected so that the distance between the pixels is great.

In the boundary smoothing step, the pixels may be selected by: a first sub-step of selecting a start pixel from the pixels in the boundary line, storing positional information of the start pixel, and selecting an end pixel which is separated from the start pixel along the boundary line by a predetermined number of pixels X; a second sub-step of determining a degree of complexity of the boundary line between the start pixel and the end pixel; and a third sub-step of storing the positional information of the end pixel, selecting the end pixel as a new start pixel, and then repeatedly performing the first sub-step when the boundary line determined in the degree of complexity in the second sub-step is not complex, and detecting an intermediate pixel separated from the start pixel along the boundary line by the number of pixels W smaller than the number of pixels between the start pixel and the end pixel, storing the positional information of the intermediate pixel, selecting the intermediate pixel as a new start pixel, and then repeatedly performing the first sub-step when the boundary line determined in the degree of complexity in the second sub-step.

In the second sub-step, the degree of complexity of the boundary line may be determined by comparing a predetermined value Z with a value z obtained by dividing the number of pixels Y in a straight line between the start pixel and the end pixel by the number of pixels X in the boundary line between the start pixel and the end pixel. Here, $W=5$, $X=20$, and $Z=0.8$.

The boundary correcting step may include: a sub-step of detecting protruded pixels by comparing slopes of the pixels in the boundary line; a sub-step of determining whether the boundary line between the adjacent protruded pixels out of the protruded pixels should be corrected; and a sub-step of correcting the boundary line using a curve generating method when it is determined that the boundary line should be corrected.

In this case, the sub-step of determining whether the boundary line should be corrected may include comparing a predetermined value K with a value k obtained by dividing the number of pixels I in the boundary line between the adjacent protruded pixels by the number of pixels J in a straight line between the adjacent protruded pixels, determining that the boundary line should be maintained when the obtained value is smaller than the predetermined value, and determining that the boundary line should be corrected when the obtained value is greater than the predetermined value, where $K=1.8$.

The sub-step of correcting the boundary line using the curve generating method may be performed by applying the curve generating method to the adjacent protruded pixels and two pixels separated outward from the adjacent protruded pixels by 30 pixels.

The region separating step may include a binarization sub-step of calculating an optimal threshold value and displaying only the lean region. The optimal threshold value may be calculated in the binarization sub-step by: analyzing a gray-scale level using a brightness distribution of an image in a green band; excluding a region where the gray-scale level of the image in the green band is less than 25 and a region where the gray-scale level is greater than 150 and reducing the gray-scale level in the remaining region to a half; calculating a probability distribution of the lean region and a probability distribution of a fat region using probability density functions of the gray-scale levels, a sum of probability density functions of the lean region, and a sum of probability density functions of the fat region; applying a probability distribution of the lean region and a probability distribution of the fat region to α-dimension Rényi entropy; calculating the gray-scale level at which the sum of the Rényi entropy in the lean region and the Rényi entropy in the fat region is the maximum; and calculating the optimal threshold value using the gray-scale level at which the sum of the Rényi entropy having three different values depending on the range of α is the maximum.

The grading region determining step may include an interactive checking sub-step of allowing a user to check the determined grading region and correcting the boundary line.

The boundary extracting step may include a labeling sub-step of labeling the lean region of which the boundary line would be extracted, a dilation sub-step of filling an empty space remaining in the labeled region, an erosion sub-step of eroding a part of the lean region exaggerated in the dilation sub-step, and an automatic boundary extracting sub-step of extracting the boundary line of the lean region determined up to the erosion sub-step.

The grading step may include at least one sub-step of a size determining sub-step of determining an area of a lean region, an intramuscular fat determining sub-step of determining a marbling state of beef, a color determining sub-step of determining lean and fat colors, and a fat thickness determining sub-step of determining a thickness of back fat.

The size determining sub-step may include converting the number of pixels of the grading region into an area.

The intramuscular fact determining sub-step may include grading the beef quality by performing a binarization process with respect to 135 using the image of the red band and by calculating tissue indexes of element difference moment, entropy, uniformity, and area ratio using four paths selected from a co-occurrence matrix as a horizontal path mask.

The color determining sub-step may use L*a*b* values of the International Commission on Illumination changed, which is obtained by converting average RGB values calculated from output values of an image expressed by RGB by learning using a back-propagation multi-layer neural network.

The thickness determining sub-step may include performing a triangular method on the grading region to detect the longest straight line in the grading region, selecting the fat part of which the thickness should be measured on the basis of the straight line, drawing a normal line perpendicular to the straight line in the selected fat region, and measuring the length of the normal line.

According to another aspect of the invention, there is provided a system for automatically grading beef quality, including: an image acquiring unit including a lamp and a CCD camera; a grading unit including an analyzer analyzing an image acquired by the image acquiring unit and grading the beef quality and a monitor displaying the image and the analysis result; and a data storage unit storing the image data and the analysis result data.

Here, the monitor may include a touch pad and the data storage unit may be connected to a computer network.

According to the invention, it is possible to automatically grade beef quality by extracting a boundary line substantially similar to a boundary line extracted by a specialized grader.

It is also possible to enhance the accuracy of the determination result and to allow a user to participate directly in the correction, by providing a user with an interactive checking procedure in the grading region determining step.

According to the invention, since the image data and the grading result data are stored in the data storage unit, the image data and the grading result data can be formed into a database. The database can allow the grading result including the measured values of grading items to be checked at any time, whereby the objectivity of the grading is guaranteed and the database can be utilized as base materials for improving meat quality of cattle farms. In addition, by applying the beef grading data according to the invention to the recent beef history rule, the database can be utilized as materials useful for selling or purchasing beef.

Particularly, by connecting the data storage unit to a computer network, it is possible to check the grading result data according to the invention at any place of the country using the Internet.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF EXEMPLARY EMBODIMENTS

Hereinafter, exemplary embodiments of the invention will be described in detail with reference to the accompanying drawings.

Figure 1:
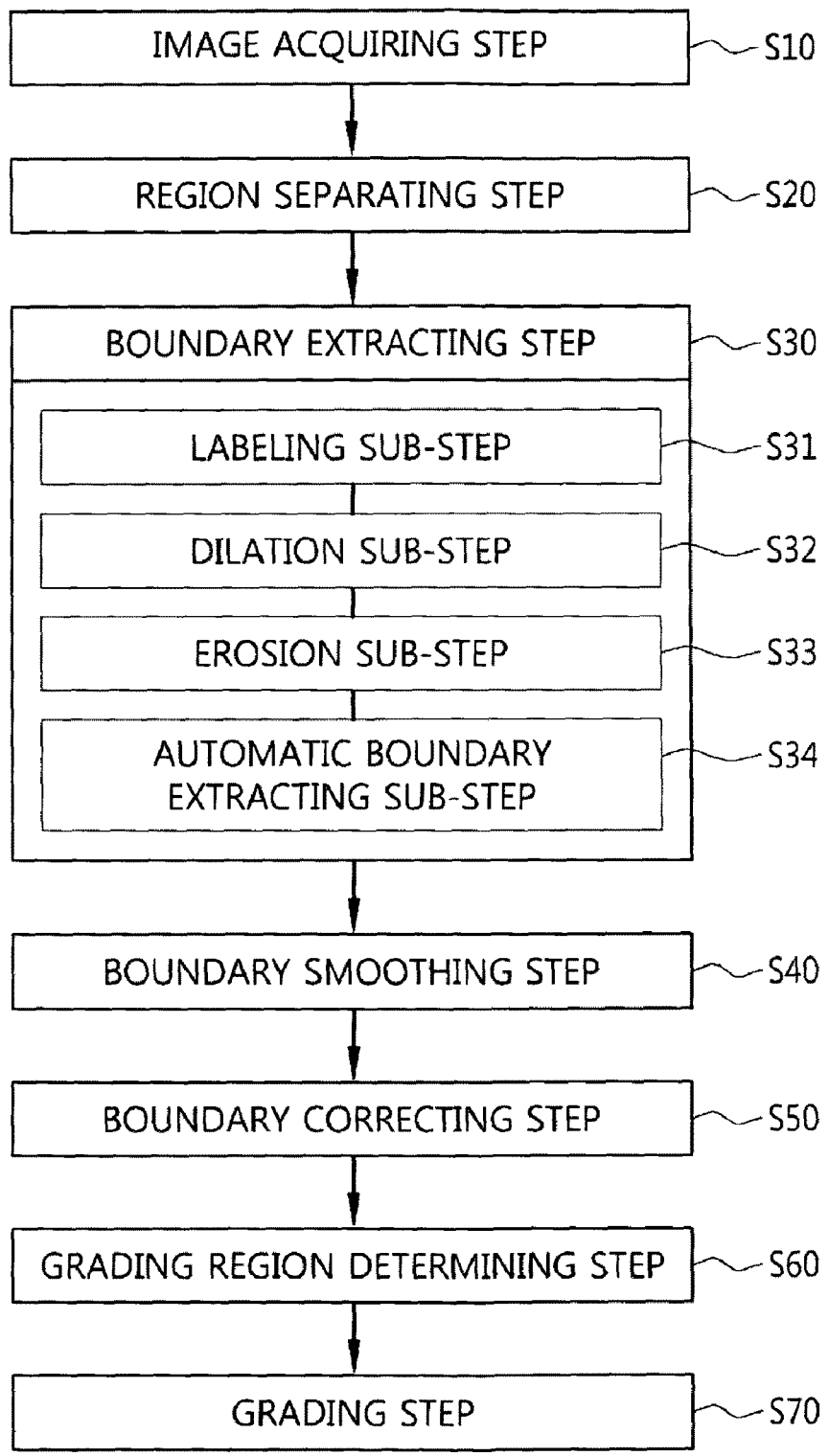
FIG. 1 is a flowchart illustrating a method of automatically grading beef quality according to an embodiment of the invention.

FIG. 1 is a diagram illustrating the flow of a method of automatically grading beef quality according to an embodiment of the invention.

The method of automatically grading beef quality according to the embodiment includes an image acquiring step S10, a region separating step S20, a boundary extracting step S30, a boundary smoothing step S40, a boundary correcting step S50, a grading region determining step S60, and a grading step S70.

In the image acquiring step S10, an image is acquired by photographing a section of beef to be graded. In general, the section used in the grading step is a section of a thirteenth rib. The acquired image is a color image captured by a CCD camera so as to enable digital analysis. Since the color of beef is very important in grading the beef quality and the color the captured image may vary due to the lamp, it is preferable that a map employing an LED is used. Particularly, when an LED lamp and a CCD camera are combined to construct an image acquiring unit which can easily move to the section of beef to be photographed, it is possible to acquire images of beef with the same lamp condition.

Figure 2:
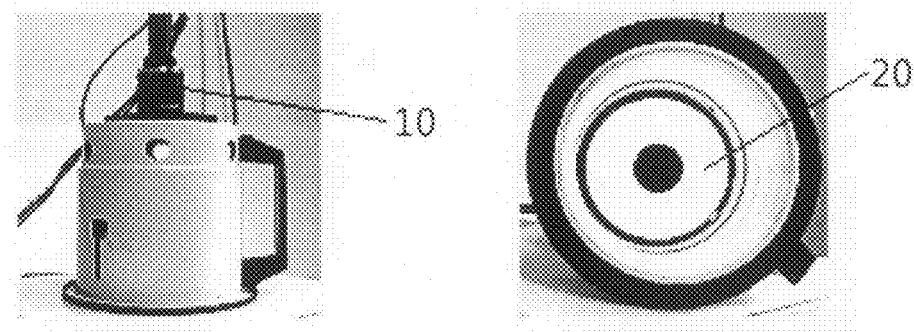
FIG. 2 is diagram illustrating an image acquiring unit including an LED lamp and a CCD camera.

FIG. 2 is a diagram illustrating an image acquiring unit including the LED lamp and the CCD camera.

In the region separating step S20, a lean region is separated from the acquired image. The beef to be graded includes fat surrounding the outer portion and lean meat located inside the fat. However, the lean portion obtained by removing the outer fat is eaten by persons and the lean portion is thus graded in quality. Accordingly, at the first time for determining a grading region to be graded in quality, the lean portion should be separated from the fat portion and the background portion.

The region separating step S20 employs a binarization process of displaying only the lean portion in white. The image captured by the CCD camera has an RGB format in which it can be divided into three images of red, green, and blue. As the process of binarizing the color image, various methods using a gray-scale level histogram which is scaled in 256 levels have been developed.

Figure 3:
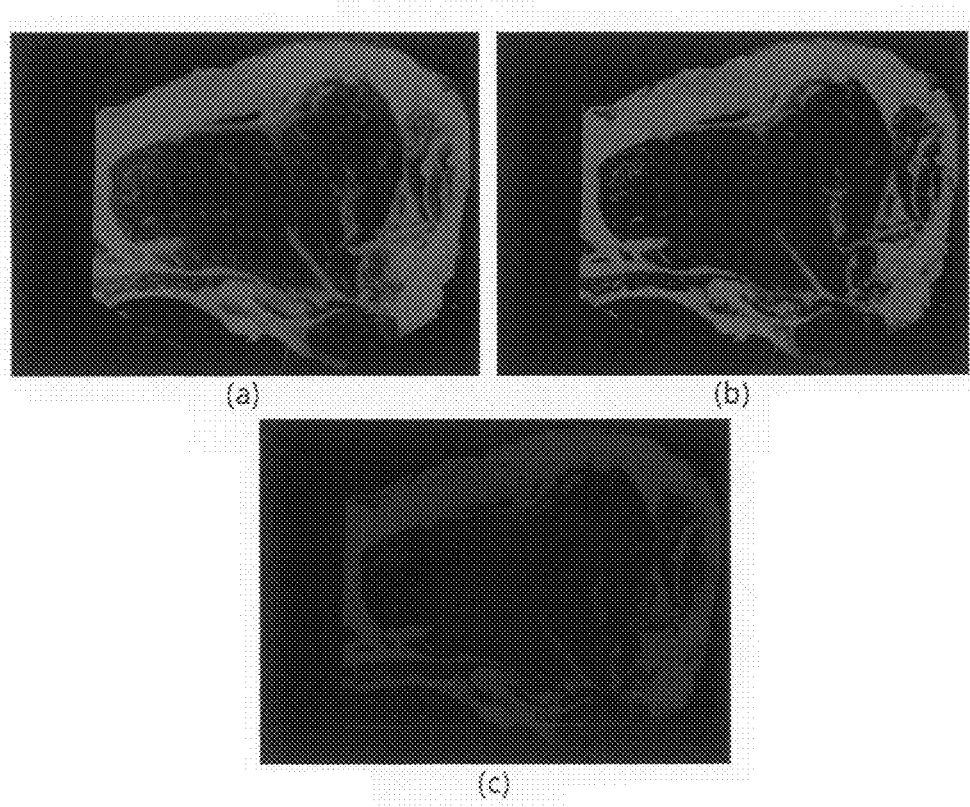
FIGS. 3A to 3C are diagrams illustrating RGB-channel images of an image captured by the CCD camera.

FIGS. 3A to 3C are diagrams RGB channel images of the image captured by the CCD camera. FIG. 3A shows an image in a red band, FIG. 3B shows an image in a green band, and FIG. 3C shows an image in a blue band.

In the past, the lean region and the fat region were separated on the basis of threshold values predetermined for the red, green, and blue images. However, in this case, the predetermined threshold values were not suitable for all the images and thus particularly threshold values should be determined for the respective images.

To solve this problem, the binarization using an entropic method has been studied. Examples of the binarization include a Re nyi entropy method, a maximum entropy method, a maximum entropy sum method, a minimum entropy method, a Tsallis method, and an entropic correlation method. However, the threshold values determined by the entropic methods were not satisfactory and the entropic methods take a much time to operate.

In this embodiment, to reduce the operation time, only a suitable one image is used and a new optimal threshold value having merits of the entropic methods.

In this embodiment, to binarize an image, a brightness distribution is analyzed using only an image in a green band most suitable for distinguishment based on the histogram.

In this analysis, first, a region having a gray-scale level less than 25 is determined and excluded as a background, and a region having a gray-scale level greater than 150 is determined and excluded as fat. Then, a process of reducing 126 gray-scale levels between the two values to 63 levels is carried out. In this embodiment, by reducing the gray-scale levels to which the entropic methods are applied, it is possible to reduce the operation time greatly. Even when about 60 gray-scale levels are used in the entropic methods, it is possible to accurately distinguish the fat and the lean from each other.

In this processes, an expression for calculating a gray-scale level $J(i,j)$ obtained by reducing the gray level $I(i,j)$ of a $(i,j)$ pixel is as follows.

$$J(i, j) = \begin{cases} 0 & \text{if } I(i, j) < r_1 \\ I(i, j)\frac{r_2 - r_1}{255} & \text{if } r_1 D I(i, j) D r_2 \\ 255 & \text{if } I(i, j) > r_2 \end{cases}$$

Here, $r_1$ is 25 determined as the background region and $r_2$ is 150 determined as the fat region. $r_1$ and $r_2$ are converted into $$L_{low} = r_1\left(\frac{r_2 - r_1}{255}\right) \text{ and } L_{high} = r_2\left(\frac{r_1 - r_2}{255}\right),$$

respectively.

The probability distribution $A_1$ of the lean region and the probability distribution $A_2$ of the fat region can be calculated as follows using probability density functions of the gray-scale levels $P_{L_{low}}$, $P_{L_{low+1}}$, $P_{L_{low+2}}$, O, $P_{L_{high}}$, the sum $p(A_1)$ of probability density functions of the lean region, and the sum $p(A_2)$ of probability density functions of the fat region.

$$A_1: \frac{P_{L_{low}}}{p(A_1)}, \frac{P_{L_{low+1}}}{p(A_1)}, 0, \frac{P_t}{p(A_1)}$$

$$A_2: \frac{P_{t+1}}{p(A_2)}, \frac{P_{t+2}}{p(A_2)}, 0, \frac{P_{L_{high}}}{p(A_2)}$$

Here, $p(A_1) = \underset{i=L_{low}}{\overset{t}{Q}} p_i$ and $p(A_2) \underset{i=t+1}{\overset{L_{high}}{Q}} p_i$, and $p(A_1)+p(A_2)=1$ i represents the gray-scale level and t represents a threshold value for distinguishing the lean and the fat.

On the other hand, the α-dimension Rēnyi entropy is defined by the following expression.

$$H_T^\alpha = \frac{1}{1-\alpha} \ln \underset{k=L_{low}}{\overset{L_{high}}{Q}} (p_k)^\alpha$$

Here, $\alpha$ ($\neq 1$) is a positive real parameter. The calculated probability distributions of the lean and the fat are applied to the Rēnyi entropy as follows.

$$H_{A_1}^{\alpha}(t) = \frac{1}{1-\alpha} \ln \sum_{i=L_{low}}^{t} \left(\frac{p_i}{p(A_1)}\right)^{\alpha},$$

$$H_{A_2}^{\alpha}(t) = \frac{1}{1-\alpha} \ln \sum_{i=t+1}^{L_{high}} \left(\frac{p_i}{p(A_2)}\right)^{\alpha}$$

Here, the gray-scale level $t^*(\alpha)$ at which $H_{A_1}^{\alpha}(t) + H_{A_2}^{\alpha}(t)$ is the maximum is expressed by the following expression.

$$t^*(\alpha) = \underset{tHG}{\text{Argmax}} \{H_{A_1}^{\alpha}(t) + H_{A_2}^{\alpha}(t)\}$$

$$t^*(\alpha) = \begin{cases} t_1^* & \text{if } 0 < \alpha < 1 \\ t_2^* & \text{if } \alpha \geq 1 \\ t_3^* & \text{if } 1 < \alpha < \wedge \end{cases}$$

Here, $t^*_1$, $t^*_2$, and $t^*_3$ are values different from each other. The gray-scale level $t^*_2$ at which $\alpha$ comes close to 1 is equal to the optimal threshold value in the maximum entropy sum method, and the gray-scale level $t^*_3$ at which $\alpha$ is greater than 1 is equal to the optimal threshold value in the entropic correlation method. The gray-scale level $t^*_1$ is a threshold value in the R ē nyi entropy method when $\alpha$ is 0.5.

Accordingly, the optimal threshold value $t^*_c$ in this embodiment is expressed by the following expression.

$$t_c^* = t_1^*\left[p(t_1^*) + \frac{1}{4}\omega\beta_1\right] + \frac{1}{4}t_2^*\omega\beta_2 + t_3^*\left[1 - p(t_3^*) + \frac{1}{4}\omega\beta_3\right]$$

Here, $p(t) = \sum_{i=L_{low}}^{t} p_i$, $\omega = p(t_3^*) - p(t_1^*)$, and $$(\beta_1, \beta_2, \beta_3) = \begin{cases} (1, 2, 1) & \text{if } |t_1^* - t_2^*|D5 \text{ and } |t_2^* - t_3^*|D5 \\ (1, 2, 1) & \text{if } |t_1^* - t_2^*| > 5 \text{ and } |t_2^* - t_3^*| > 5 \\ (0, 1, 3) & \text{if } |t_1^* - t_2^*|D5 \text{ and } |t_2^* - t_3^*| > 5 \\ (3, 1, 0) & \text{if } |t_1^* - t_2^*| > 5 \text{ and } |t_2^* - t_3^*|D5. \end{cases}$$

The image in the green band is binarized using the optimal threshold value calculated in the above-mentioned method.

Figure 4:
FIG. 4 is a diagram illustrating an image obtained by binarizing an image of a green band using the optimal threshold value acquired in an embodiment of the invention.

FIG. 4 is a diagram illustrating an image obtained by binarizing the image in the green band using the calculated optimal threshold value according to the embodiment.

In the boundary extracting step S30, a boundary line of the lean region is extracted. That is, the boundary line of the lean region marked with white by the binarization process is extracted. Here, the outline of a binarized image can be extracted by various methods, many of which are automated. However, in the image having been subjected to the region separating step S20, the fat portions in the lean region are empty and small lean portions are displayed in addition to a large lean blob. Accordingly, when the automatic outline extracting method is applied at once, the boundary line of the lean region necessary to determine the grading region cannot be extracted. Therefore, in this embodiment, an automatic boundary extracting sub-step 34 is performed after a labeling sub-step S31, a dilation sub-step S32, and an erosion sub-step S33 are performed.

In the labeling sub-step S31, a blob labeling process is performed on the binarized image to label the lean region from which the boundary line should be extracted. The blob labeling process is performed on pixels connected in eight directions to each pixel, whereby only the principal lean blobs remain and the lean regions including much fat so as not to be used are removed.

Figure 5:
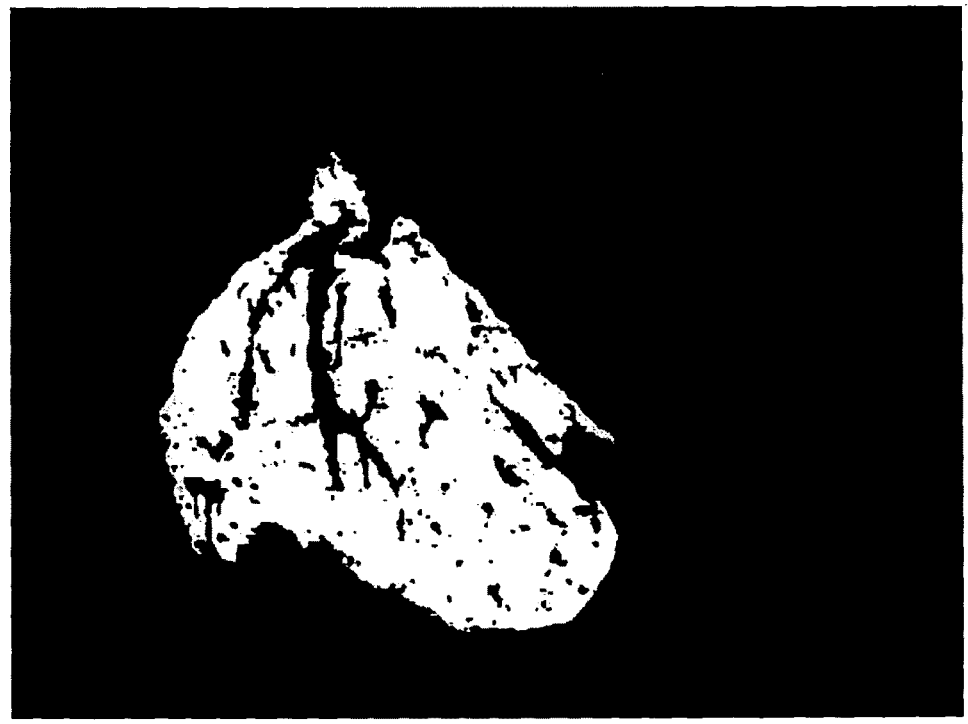
FIG. 5 is a diagram illustrating an image of only a blob of a lean region obtained by labeling the image shown in FIG. 4.

FIG. 5 is a diagram illustrating an image in which only the lean blobs remain by labeling the image shown in FIG. 4.

In the dilation sub-step S32, empty spaces resulting from intramuscular fat located in the lean blobs having been the labeling sub-step are filled. In this embodiment, the insides of the lean regions are filled by twice dilation sub-steps using a square mask of 5×5.

Figure 6:
FIGS. 6 and 7 are diagrams illustrating images obtained by filling the blob of the image shown in FIG. 5 in a dilation sub-step.
Figure 7:

FIGS. 6 and 7 are diagrams illustrating images obtained by filling the blobs in the image shown in FIG. 5 by the dilation sub-step.

In the erosion sub-step S33, the blobs of the lean regions exaggerated in the dilation sub-step are reduced. In this embodiment, the erosion sub-step is performed using a square mask of 5×5.

Figure 8:
FIG. 8 is a diagram illustrating an image obtained by performing an erosion sub-step on the image shown in FIG. 7.

FIG. 8 is a diagram illustrating an image obtained by performing the erosion sub-step on the image shown in FIG. 7.

In the automatic boundary extracting sub-step S34, the boundary line of the lean region trimmed in the dilation sub-step and the erosion sub-step is extracted using an automatic boundary extracting method. In this embodiment, the boundary line of the lean blob is extracted using an 8-direction chain coding method.

Figure 9:
FIG. 9 is a diagram illustrating an image obtained by performing an automatic boundary extracting sub-step on the image shown in FIG. 8.

FIG. 9 is a diagram illustrating an image obtained by performing the automatic boundary extracting sub-step on the image shown in FIG. 8.

In the boundary smoothing step S40, the boundary line of the lean region is smoothed. Since the boundary line extracted in the boundary extracting step S30 is extracted in the unit of pixels, the boundary line is much rugged and is different from the boundary line extracted by a specialized grader. Accordingly, the boundary line has to be smoothed so as to be similar to the boundary line extracted by the specialized grader.

Figure 10:
FIG. 10 is a diagram illustrating a boundary line before it is subjected to a boundary smoothing step.

FIG. 10 is a diagram illustrating the boundary line not having been subjected to the boundary smoothing step.

In the boundary smoothing step S40, specific pixels are extracted from the boundary line and then a curve generating method using relationships of the extracted pixels are applied.

The pixels for generating a curve are extracted so that a distance between the pixels is great in a part with a smooth boundary line, and the pixels are extracted so that the distance between the pixels is small in a part with a rugged boundary line. That is, the part with the smooth boundary line and the part with the complex boundary line should be distinguished. In this embodiment, the number of pixels Y in a straight line between two pixels A and B is compared with the number of pixels X in the boundary line between the two pixels A and B, thereby determining the degree of complexity of the boundary line. For example, when X between two pixels A and B separated by 20 pixels along the boundary line is 20 and Y is also 20 when the boundary line between the two pixels A and B is a straight line which is the smoothest line. The value of Y decreases as the complexity of the boundary line between A and B increases. Accordingly, z defined as a value obtained by dividing Y by X can be used as a coefficient indicating the degree of complexity of the boundary line between two pixels. When z is greater than a predetermined value Z, the boundary line can be determined as a smooth line. When z is smaller than the predetermined value, the boundary line can be determined as a complex line. The pixel extracting process using that is described below.

First, a start pixel A in the boundary line is selected, the positional information of the start pixel is stored, and an end pixel B separated from the start pixel by X along the boundary line is detected.

The distance Y in the straight line between A and B is divided by X to acquire z and the value of z is compared with the predetermined value Z.

When z is equal to or greater than Z, the positional information of the pixel B is stored and the above-mentioned entire processes are repeatedly performed using the pixel B as a new start pixel.

When z is smaller than Z, the positional information of an intermediate pixel C separated from the pixel A by W (<X) along the boundary line is stored and the above-mentioned processes are repeatedly performed using the intermediate pixel X as a new start pixel.

In this course, X and Z are predetermined values, and the pixels to be extracted are changed depending on the values. In this embodiment, W=5, X=20, and Z=0.8 are used.

By carrying out the curve generating method using the positional information of the extracted pixels, it is possible to obtain a smoothed boundary line. In this embodiment, an Overhauser curve generating method is used.

Figure 11:
FIG. 11 is a diagram illustrating the boundary line after the boundary smoothing step according to the embodiment is performed on the boundary line shown in FIG. 10.

FIG. 11 is a diagram illustrating an image of the boundary line obtained by performing the boundary smoothing step according to this embodiment on the boundary line shown in FIG. 10.

In the boundary correcting step S50, protruded portions and indented portions of the boundary line which are not smoothed in the boundary smoothing step S40 are corrected. In the boundary smoothing step S40, since pixels are extracted in the unit of small pixels and the curve generating method is applied, valley portions indented by fat or steeply protruding portions remain after the boundary smoothing step.

Figure 12:
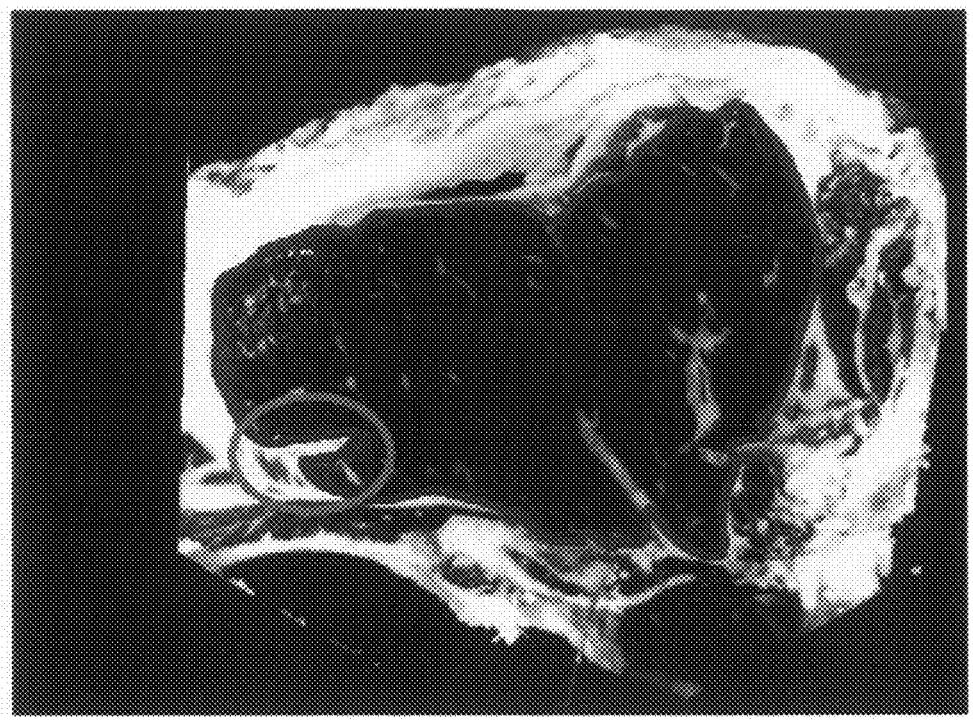
FIG. 12 is a diagram illustrating the boundary line of a lean region extracted from beef including a valley portion formed by fat.
Figure 13:
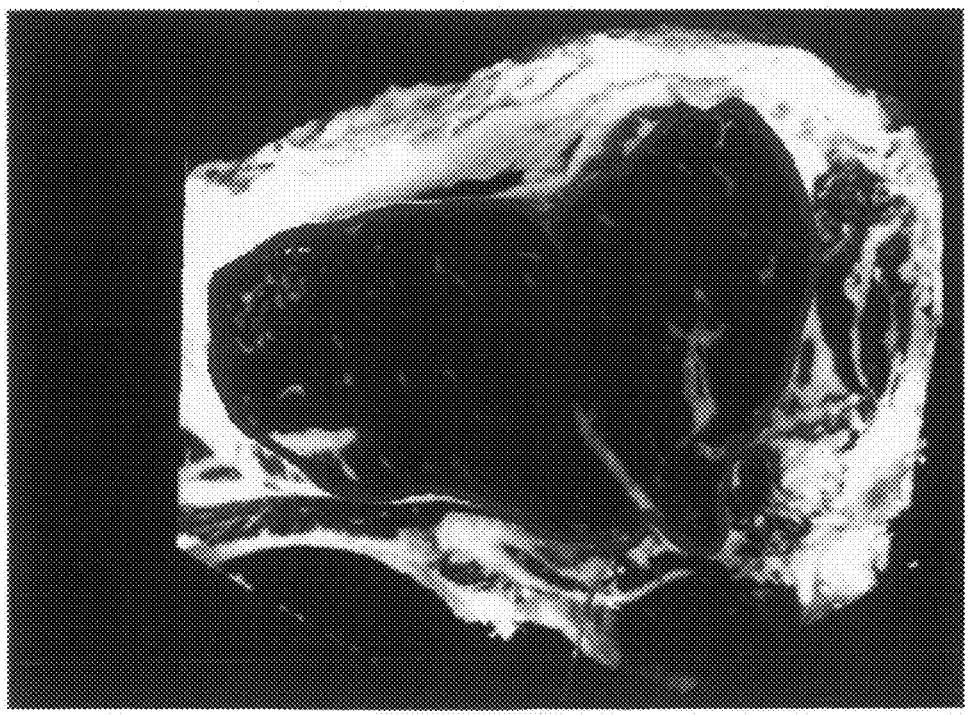
FIG. 13 is a diagram illustrating the boundary line obtained by performing the boundary smoothing step according to the embodiment on the image shown in FIG. 12.

FIG. 12 is a diagram illustrating an image of the boundary line of the lean region extracted from beef including the valley portions indented by the fat. FIG. 13 is a diagram illustrating an image of the boundary line obtained by performing the boundary smoothing step according to this embodiment on the image shown in FIG. 12.

Some protruded portions or indented portions may not be cut along the boundary in the actual cutting operation as shown in FIG. 12 and the specialized graders generally set the grading region to include these portions. Accordingly, a correction step of correcting small-sized indented portions or protruded portions has to be performed.

To correct the indented portions or the protruded portions, the indented portions or the protruded portions should be first determined. Since a protruded portion is formed at the entry of the indented portion, the protruded portions are first detected in the boundary line in this embodiment. The protruded pixels are detected by comparing the slopes of the pixels along the boundary line.

Figure 14:
FIG. 14 is a diagram illustrating an image in which protrusions are marked in the boundary line including indented portions.

FIG. 14 is a diagram illustrating an image in which the protruded portions are marked in the boundary line including the concave portions.

It is then determined whether the boundary between the adjacent protruded pixels should be corrected. This determination is made on the basis of a value k obtained by dividing the number of pixels I in the boundary line between the adjacent protruded pixels by the number of pixels J in the straight line between the protruded pixels. When the value of k is smaller than a predetermined value K, the boundary line is maintained. When the value of k is greater than the predetermined value K, the boundary line is corrected on the basis of the adjacent protruded pixels.

Figure 15:
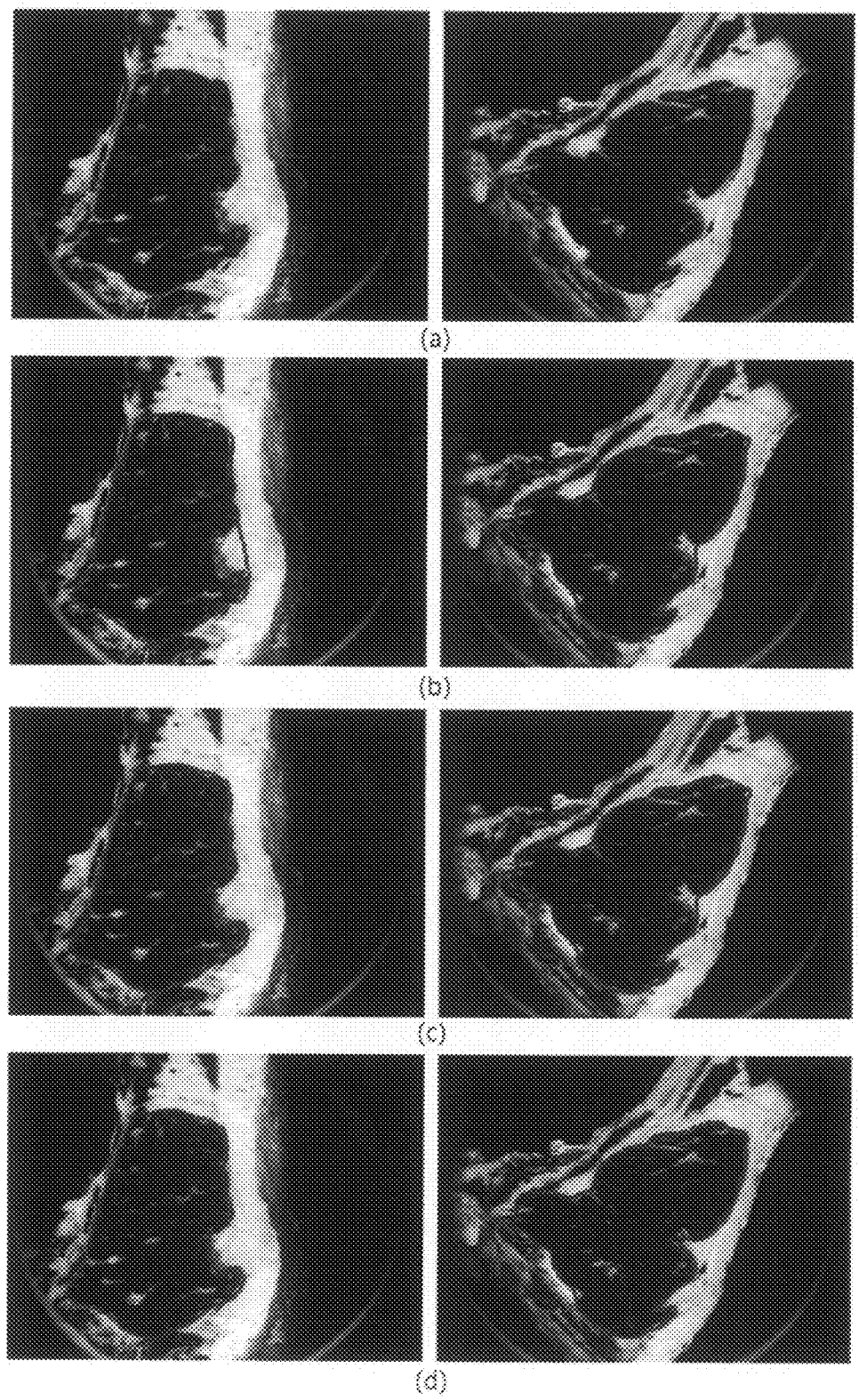
FIGS. 15A to 15D are diagrams showing differences between the boundary lines corrected depending on a value of K.

FIGS. 15A to 15D are diagrams illustrating images in which the boundary line is corrected different depending on the value of K. FIG. 15A shows an originally photographed picture, FIG. 15B shows the corrected boundary line when the value of K is set to 1.6, FIG. 15C shows the corrected boundary line when the value of K is set to 1.8, and FIG. 15D shows the corrected boundary line when the value of K is set to 2.1. It can be seen from the drawings that the boundary line is less corrected as the value of K becomes greater. The boundary line of the large indented portion in the left beef image need not to be corrected and the boundary line of the small indented portion in the right beef image need to be corrected. Accordingly, it can be seen that the optimal value of K is 1.8.

The method of correcting the boundary line on the basis of the protruded pixels employs the curve generating method, particularly, the Overhauser curve generating method. To correct the boundary line using the Overhauser curve generating method, two adjacent protruded pixels p2 and p3 and two pixels p1 and p4 separated outward from the pixels p2 and p3 by a predetermined number of pixels along the boundary line are extracted. In this embodiment, the pixels separated from the pixels p2 and p3 by 30 pixels are extracted as p1 and p4. Four pixels p1, p2, p3, and p4 extracted in this way are used in the Overhauser curve generating method to correct the boundary line between the protruded pixels. The Overhauser curve C(t) is generated by the following expression.

$$C(t) = [a][b][c]$$

$$[a] = [t^3, t^2, t, 1], \quad [b] = \begin{vmatrix} -0.5 & 1.5 & -1.5 & 0.5 \\ 1 & -2.5 & 2 & -0.5 \\ -0.5 & 0 & 0.5 & 0 \\ 0 & 1 & 0 & 0 \end{vmatrix}, \quad [c] = \begin{vmatrix} p_1 \\ p_2 \\ p_3 \\ p_4 \end{vmatrix}$$

Here, t is 0 for p2 and 1 for p3.

Figure 16:
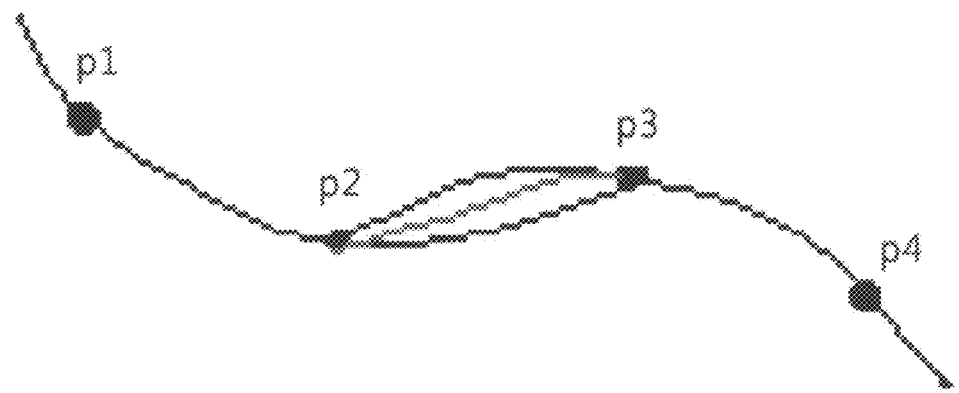
FIG. 16 is a diagram illustrating a curve obtained by correcting the boundary line between adjacent protruded pixels p2 and p3 using an Overhauser curve generating method.

FIG. 16 is a diagram illustrating the process of correcting the boundary line between the adjacent protruded pixels p2 and p3 using the Overhauser curve generating method.

The accuracy of the boundary line determined as described above can be expressed by PLM (Percent of Lean-tissue Match).

$$PLM = \frac{\sum_{i}^{M}\sum_{j}^{N}[(D(i, j) \mid C(i, j))]}{\sum_{i}^{M}\sum_{j}^{N}[C(i, j)]} s100$$

Here, D(i,j) represents a region surrounded by a desirable boundary line extracted by specialized graders, C(i,j) represents a region surrounded by the boundary line extracted in this embodiment, and PLM represents the degree of overlapping between D(i,j) and C(i,j).

The percent error (PE) of the extracted boundary line is calculated by PE=100−PLM. However, this value does not express the case where C(i,j) is not included in D(i,j).

Therefore, an AEPD (Average Error Pixel Distance) indicating the difference between the two results is applied together.

$$AEPD = \frac{\overset{M\,N}{QQ}XOR[(D(i,\,j)\mid C(i,\,j))]}{\underset{i\ j}{\overset{M\,N}{QQ}}[P(i,\,j)]}$$

Here, XOR represents the exclusive OR, is 1 when a difference exists in background or boundary line, and is 0 when a difference hardly exists in background or boundary line. $P(i,j)$ represents the outline of $D(i,j)$.

Table 1 shows the accuracies of the boundary lines extracted in this embodiment.

TABLE 1

| Sample | C(i, j) | D(i, j) | A(i, j) | PE(%) | AEPD |
|---|---|---|---|---|---|
| 1 | 62,786 | 61,796 | 61,603 | 1.88 | 1.55 |
| 2 | 53,271 | 53,164 | 52,367 | 1.7 | 1.83 |
| 3 | 50,847 | 49,817 | 49,472 | 2.7 | 2.07 |
| 4 | 64,754 | 64,789 | 64,080 | 1.04 | 1.39 |
| 5 | 64,538 | 61,029 | 60,748 | 5.87 | 4.3 |
| 6 | 69,848 | 66,752 | 66,314 | 5.06 | 3.6 |
| 7 | 69,749 | 69,012 | 68,613 | 1.31 | 1.48 |
| 8 | 61,879 | 61,058 | 60,869 | 1.63 | 1.25 |
| 9 | 67,154 | 66,920 | 66,557 | 0.89 | 1.03 |
| 10 | 72,634 | 68,004 | 67,270 | 7.38 | 4.49 |
| 11 | 70,604 | 69,718 | 68,737 | 2.64 | 2.34 |
| 12 | 79,267 | 78,767 | 77,839 | 1.80 | 1.9 |
| 13 | 75,864 | 75,365 | 74,276 | 2.09 | 2.21 |
| 14 | 69,592 | 70,361 | 68,509 | 1.56 | 2.13 |
| 15 | 90,292 | 89,256 | 88,718 | 1.74 | 1.44 |
| 16 | 89,479 | 87,610 | 87,378 | 2.35 | 1.65 |
| 17 | 106,399 | 104,688 | 103,268 | 2.94 | 3.16 |
| 18 | 80,534 | 79,132 | 78,796 | 2.16 | 1.54 |
| 19 | 85,135 | 79,186 | 79,072 | 7.12 | 4.8 |
| 20 | 77,111 | 73,834 | 73,200 | 5.07 | 3.66 |
| 21 | 75,434 | 74,613 | 74,165 | 1.68 | 1.43 |
| 22 | 78,753 | 77,401 | 76,960 | 2.28 | 1.67 |
| 23 | 75,724 | 74,405 | 73,544 | 2.88 | 2.25 |
| 24 | 76,001 | 77,064 | 74,507 | 1.97 | 3.53 |
| 25 | 75,186 | 73,509 | 72,969 | 2.95 | 2.49 |
| 26 | 78,864 | 77,744 | 76,865 | 2.53 | 2.14 |
| 27 | 80,846 | 79,205 | 78,900 | 2.41 | 1.83 |
| 28 | 72,868 | 71,799 | 71,318 | 2.13 | 1.65 |
| 29 | 60,475 | 61,589 | 59,556 | 1.52 | 2.45 |
| 30 | 65,447 | 65,601 | 64,349 | 1.68 | 1.92 |
| 31 | 82,916 | 82,044 | 81,570 | 1.62 | 1.64 |
| 32 | 70,181 | 69,893 | 69,426 | 1.08 | 1.27 |
| 33 | 66,897 | 68,771 | 65,926 | 1.45 | 3.66 |
| 34 | 71,344 | 68,982 | 67,815 | 4.95 | 4.74 |
| 35 | 71,732 | 72,631 | 70,789 | 1.32 | 2.77 |
| 36 | 68,476 | 71,414 | 66,172 | 3.37 | 7.13 |

Here, $A(i,j)=D(i,j)iC(i,j)$ and the units of $D(i,j)$, $C(i,j)$, and $A(i,j)$ are pixels.

In the table, the PE of the boundary lines extracted in this embodiment has an average value of 2.63, a maximum value of 7.38, and a minimum value of 0.89. The AEPD has an average value of 2.51, a maximum value of 7.13, and a minimum value of 1.03.

It can be seen from the table that the boundary lines of the lean regions extracted according to this embodiment are very similar to the desirable boundary lines extracted by the specialized graders and can be applied as the boundary lines of the regions to be automatically graded.

In the grading region determining step S60, a grading region to be graded is determined on the basis of the smoothed and corrected boundary line. The grading region can be determined automatically in a grading system, but it is preferable that a user check the determined grading region. Particularly, an interactive checking course allowing the user to correct the boundary line is preferably disposed in the course of checking. In this case, by providing a touch panel as a monitor displaying an image, the user can be allowed to directly input a correction point to the image displayed on the monitor. At the time of correcting the boundary line, the user can directly input a corrected boundary line with the touch panel, or can input a correction point with a pointer or the like and apply the Overhauser curve generating method.

In the grading step S70, the beef quality is graded on the basis of the determined grading region. The specialized graders synthetically consider the size of a lean portion, the distribution of intramuscular fat, the fat and lean colors, and the back fat thickness to grade the beef quality.

In the size determining sub-step, an area of a lean portion is determined by converting the number of pixels in the determined grading region into an area.

In general, in the intramuscular fat determining sub-step, the distribution of the intramuscular fat which is expressed by "marbling" is determined. For this purpose, a co-occurrence matrix is calculated from the image of the lean region. The binarization process is performed using the image in the red band out of the RGB channels of the image of the lean region. Four paths are selected as a horizontal path mask from the co-occurrence matrix. Then, four tissue indexes of element difference moment (EDM), entropy (ENT), uniformity (UNF), and area ratio (AR) are calculated therefrom. The four tissue indexes are calculated as follows.

$$EDM: \underset{i\ j}{QQ}(i-j)C_{ij}$$

$$ENT: \underset{i\ j}{QQ}C_{ij}$$

$$UNF: \underset{i\ j}{QQ}C_{ij}^2$$

AR:(fat area)/(lean area)×100(%)

Here, i and j represent positional information values of a pixel.

Figure 17:
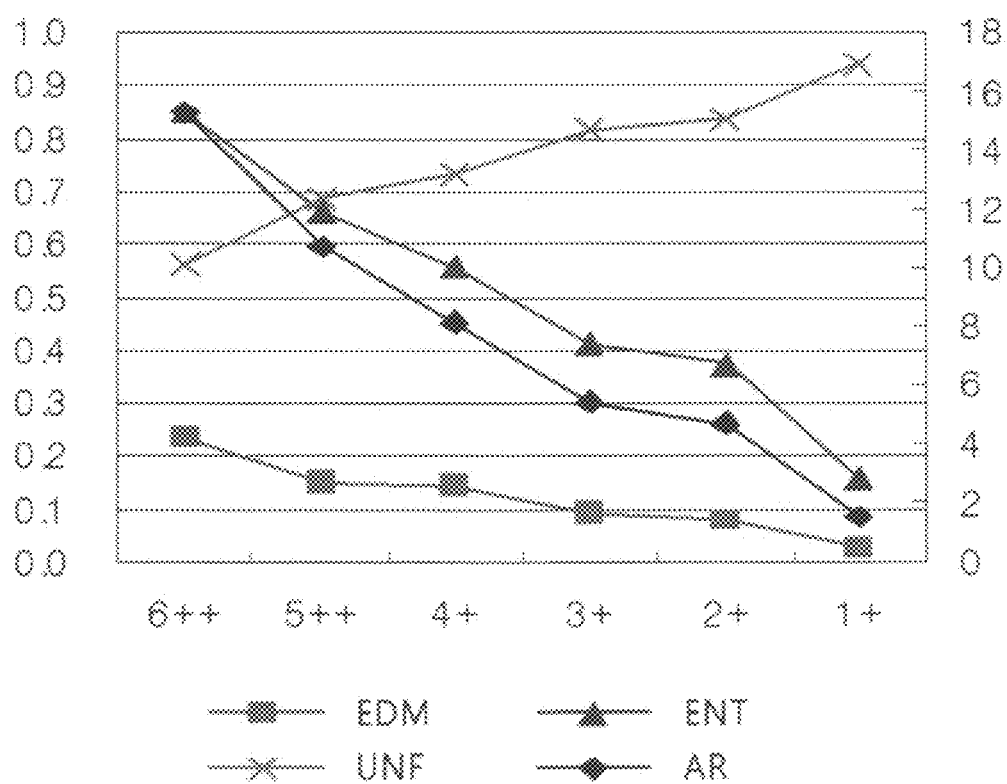
FIG. 17 is a graph illustrating grades of beef based on four tissue indexes.

FIG. 17 is a graph illustrating beef grades based on the four tissue indexes. This reflects the fact that the beef grade is higher as the element difference moment, the entropy, and the area ratio become smaller and the beef grad is higher as the uniformity becomes greater.

In the color determining sub-step, the state of beef is checked using the lean color and the fat color. Here, various lean and fat colors of samples are compared with colors of the image. However, the RGB color system of the image may not give a constant result due to the influence of the lamp or the like. The L*a*b* color system of the International Commission on Illumination (CIE) may be used instead of the RGB color system having the above-mentioned problem. The L*a*b* color values are generally measured using a colorimeter. An error may occur when the image captured by the CCD camera is converted into the L*a*b* color values using a conversion expression. Accordingly, in this embodiment, the average RGB values calculated from the output values of the color camera which are expressed in RGB are converted into the L*a*b* color values of the CIE by the learning of a neural network, and a back-propagation multi-layer neural network is used as the neural network.

In the fat thickness determining sub-step, the thickness of a back fat which is attached to the outside of the lean region is measured to grade the beef quality. First, a triangular method is performed using the protruded portions of the determined boundary line as vertexes and then the longest straight line is detected from the straight lines connecting the protruded portions. The back fat portion of which the thickness should be measured is selected from the fat layers surrounding the lean region using the selected straight line. Finally, the normal line perpendicular to the longest straight line is drawn on the back fat, and the length of the normal line is measured and is determined as the back fat thickness.

Figure 18:
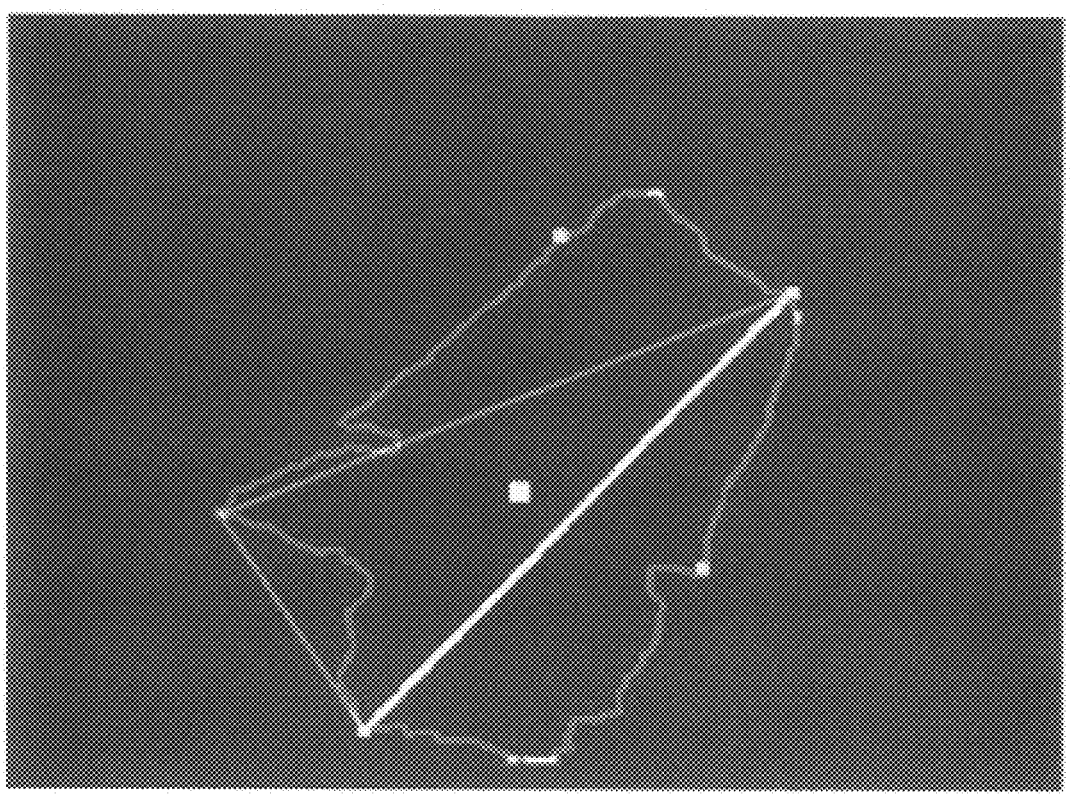
FIGS. 18 to 20 are diagrams a procedure of measuring a back fat thickness.
Figure 19:
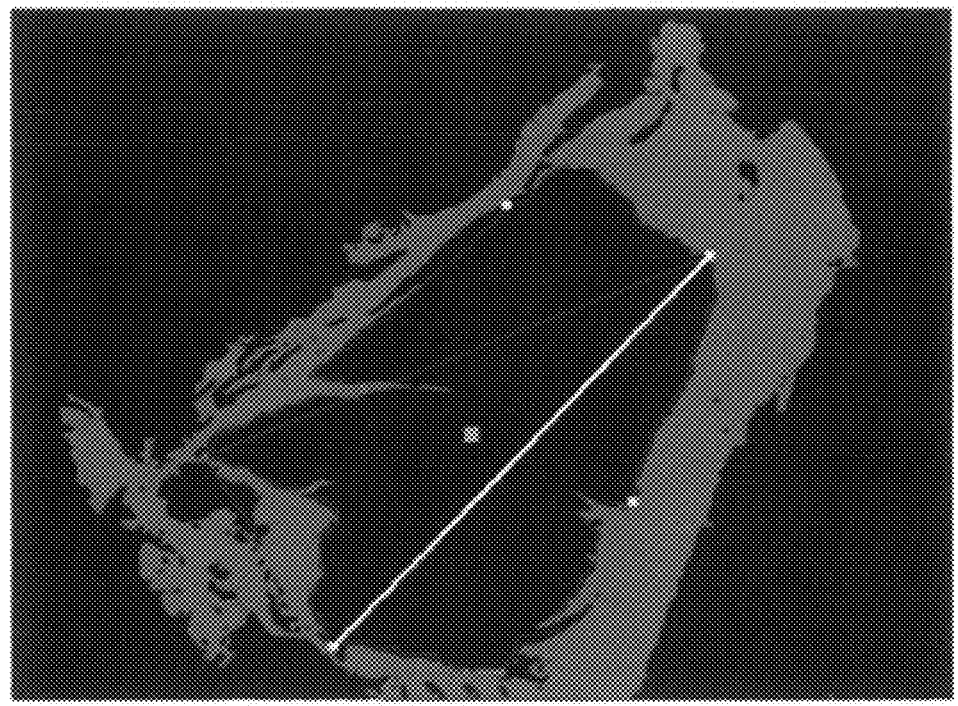
Figure 20:
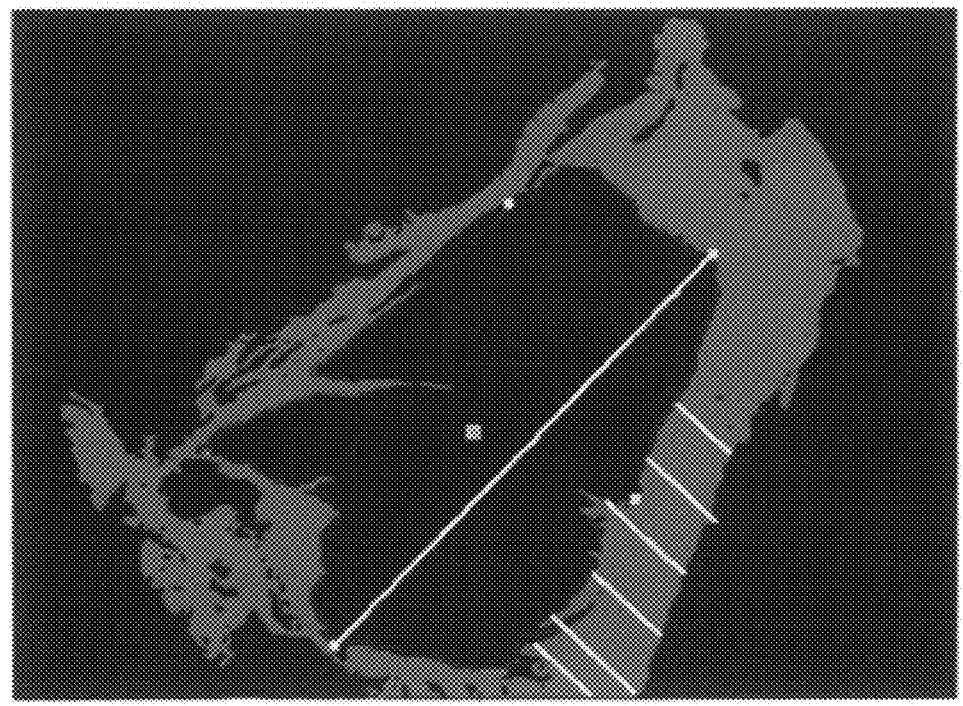

FIGS. 18 to 20 are diagrams illustrating the procedure of measuring the back fat thickness. FIG. 18 shows a state where the triangular method is applied to the grading region, FIG. 19 shows a state where the longest straight line is detected to select the back fat portion, and FIG. 20 shows a state where the back fat thickness is measured using the normal line.

The beef quality is finally graded by synthesizing the grades estimated on the basis of the size of the lean portion, the intramuscular fat distribution, the lean and fat colors, and the back fat thickness.

The system for automatically grading beef quality according to an embodiment of the invention includes an image acquiring unit, a grading unit, and a data storage unit.

The image acquiring unit serves to capture an image of a beef section and includes a CCD camera and a lamp. The CCD camera is an image capturing device which can store a beef section as a digital image, and the lamp is a device illuminating the beef with strong light so as for the CCD camera to capture an accurate image. In the image acquiring unit shown in FIG. 2 according to this embodiment, a white LED lamp 20 is attached to the periphery of the CCD camera 10 in a round form, and a knob with a switch is attached to the outside thereof, so that an image of a beef section can be easily captured.

The grading unit includes an analyzer analyzing the image acquired by the image acquiring unit to grade the beef quality and a monitor displaying the image and the analysis result.

The analyzer serves to analyze a digital image to determine a grading region and to grade the beef quality, and includes a processor analyzing the digital image.

The monitor is an imaging device displaying the image acquired by the image acquiring unit and the analysis result of the image for the user. In this embodiment, an interactive system can be constructed using a touch pad monitor to which a user can directly input data with a screen.

Figure 21:
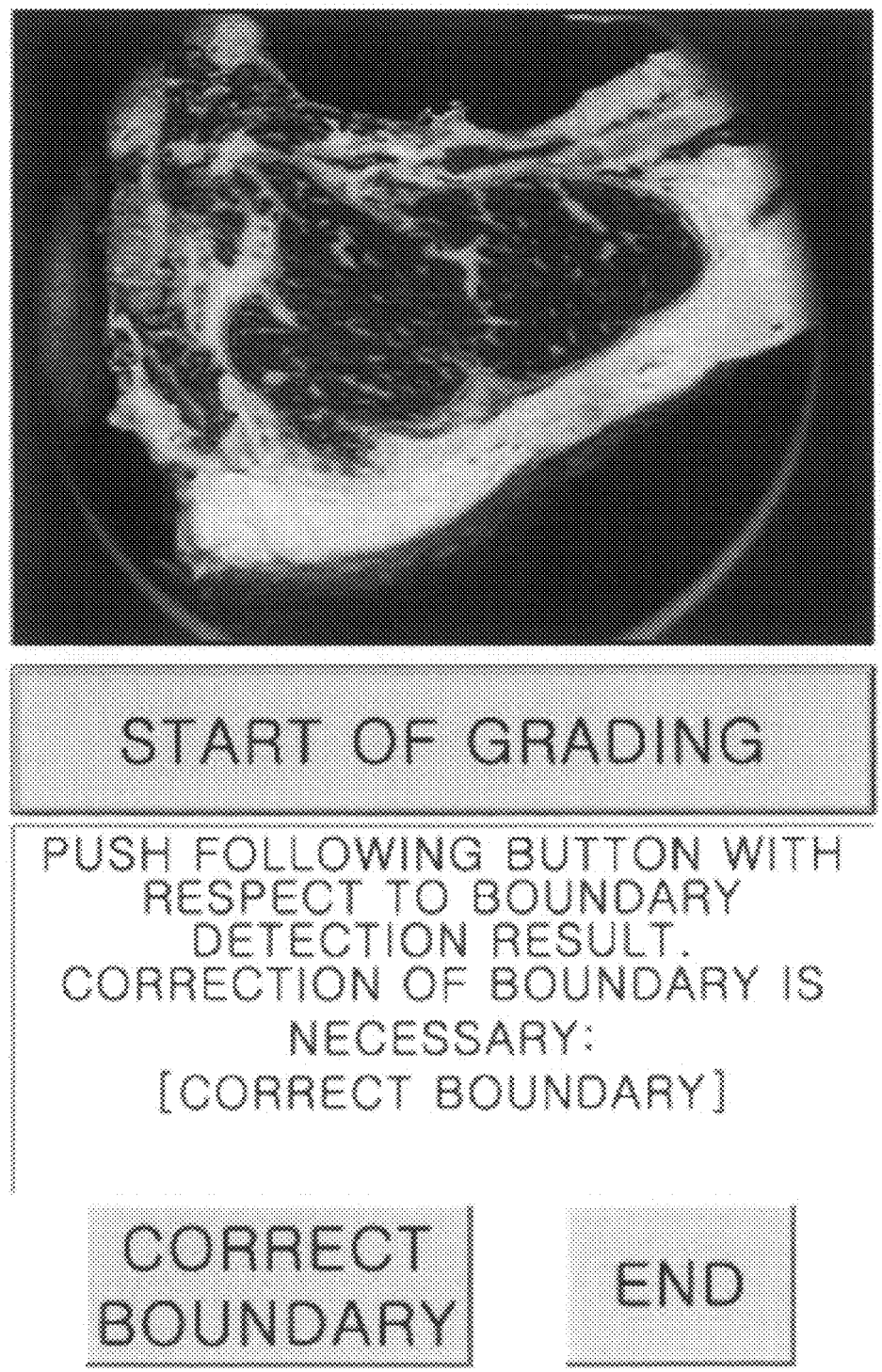
FIG. 21 is a diagram illustrating a grading start picture displayed on a monitor of a system for automatically grading beef quality according to an embodiment of the invention.

FIG. 21 is a diagram illustrating a grading start picture displayed on the monitor of the system for automatically grading beef quality according to this embodiment. In the grading start picture, a user can check the boundary line marked in the image and touch a start button, thereby allowing the analyzer to start the grading. When it is necessary to correct the boundary line marked in the image, a boundary correction button may be touched to start the correction step. In this embodiment, since the touch pad is employed, the user can directly input a correcting part to the image displayed on the monitor.

Figure 22:
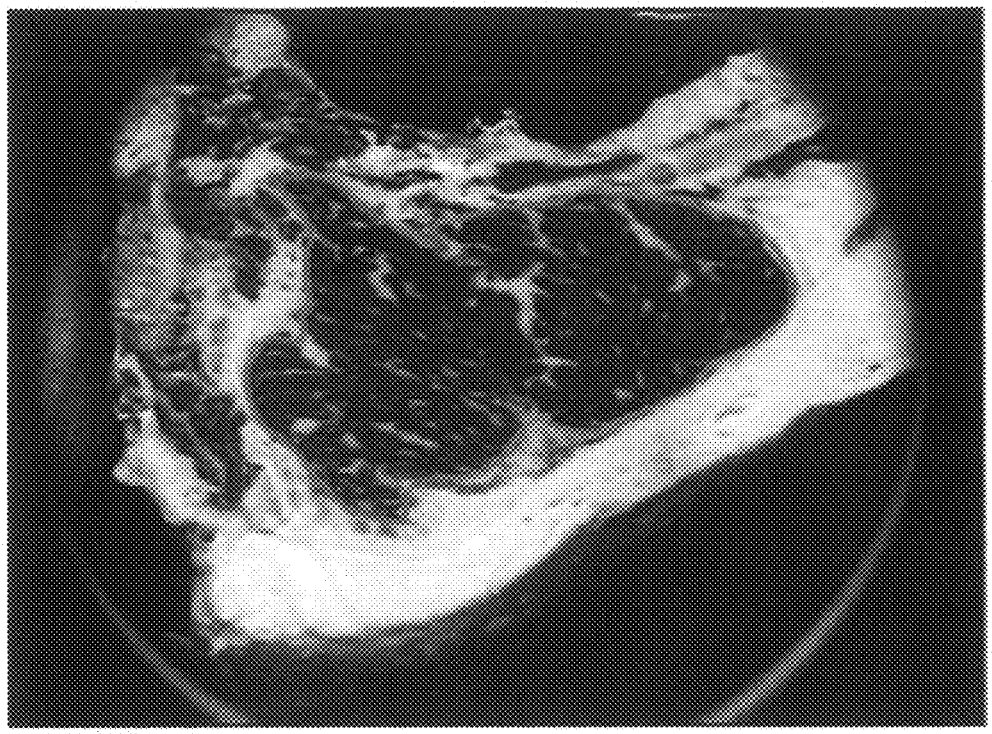
FIG. 22 is a diagram illustrating a grading result picture displayed on the monitor of the system for automatically grading beef quality according to the embodiment of the invention.

FIG. 22 is a diagram illustrating a grading result picture displayed on the monitor of the system for automatically grading beef quality according to this embodiment. Since the grading result picture includes a beef section image and the grading result, the user can see all information on the grading.

The data storage unit serves to store the image data acquired by the image acquiring unit and the analysis result data including the boundary line information analyzed by the grading unit. Since the procedures of the system according to the embodiment are all computerized, the image data and the analysis result data can be stored in the data storage unit. When the result picture shown in FIG. 22 is stored in the data storage unit to construct a database, it is possible to check the grading result including the measured values of grading items at any time, whereby the objectivity of the grading is guaranteed and the database can be utilized as base materials for improving meat quality of cattle farms. In addition, by applying the beef grading data according to the invention to the recent beef history rule, the database can be utilized as materials useful for selling or purchasing beef.

Particularly, since the data storage unit according to the embodiment is connected to a computer network, it is possible to check the analysis result data of the beef grading according to the invention at any place of the country using the Internet.

While the exemplary embodiments of the invention have been shown and described above, the invention is not limited to the exemplary embodiments, but it will be understood by those skilled in the art that the invention can be modified in various forms without departing from the technical spirit of the invention. Therefore, the scope of the invention is not limited to any specific embodiment, but should be determined by the appended claims.

What is claimed is:

1. A method of automatically grading beef quality, comprising:
    an image acquiring step of acquiring a color image of beef using a CCD camera;
    a region separating step of separating a lean region from the acquired image;
    a boundary extracting step of extracting a boundary line of the lean region;
    a boundary smoothing step of smoothing the boundary line extracted in the boundary extracting step;
    a boundary correcting step of correcting an indented portion and a protruded portion included in the boundary line having been subjected to the boundary smoothing step;
    a grading region determining step of determining a grading region on the basis of the boundary line corrected in the boundary correcting step; and
    a grading step of grading the beef quality on the basis of the image of the grading region.

2. The method according to claim 1, wherein the boundary smoothing step employs a curve generating method using relationships of pixels selected from pixels in the boundary line, and
    wherein the pixels in a part with a complex boundary line are selected so that a distance between the pixels is small, and the pixels in a part with a smooth boundary line are selected so that the distance between the pixels is great.

3. The method according to claim 2, wherein the pixels are selected in the boundary smoothing step by:
    a first sub-step of selecting a start pixel from the pixels in the boundary line, storing positional information of the start pixel, and selecting an end pixel which is separated from the start pixel along the boundary line by a predetermined number of pixels X;
    a second sub-step of determining a degree of complexity of the boundary line between the start pixel and the end pixel; and
    a third sub-step of storing the positional information of the end pixel, selecting the end pixel as a new start pixel, and then repeatedly performing the first sub-step when the boundary line determined in the degree of complexity in the second sub-step is not complex, and detecting an intermediate pixel separated from the start pixel along the boundary line by the number of pixels W smaller than the number of pixels between the start pixel and the end pixel, storing the positional information of the intermediate pixel, selecting the intermediate pixel as a new start pixel, and then repeatedly performing the first sub-step when the boundary line determined in the degree of complexity in the second sub-step.

4. The method according to claim 3, wherein the degree of complexity of the boundary line is determined in the second sub-step by comparing a predetermined value Z with a value z obtained by dividing the number of pixels Y in a straight line between the start pixel and the end pixel by the number of pixels X in the boundary line between the start pixel and the end pixel.

5. The method according to claim 4, wherein W=5, X=20, and Z=0.8.

6. The method according to claim 1, wherein the boundary correcting step includes:
a sub-step of detecting protruded pixels by comparing slopes of the pixels in the boundary line;
a sub-step of determining whether the boundary line between the adjacent protruded pixels out of the protruded pixels should be corrected; and
a sub-step of correcting the boundary line using a curve generating method when it is determined that the boundary line should be corrected.

7. The method according to claim 6, wherein the sub-step of determining whether the boundary line should be corrected includes comparing a predetermined value K with a value k obtained by dividing the number of pixels I in the boundary line between the adjacent protruded pixels by the number of pixels J in a straight line between the adjacent protruded pixels, determining that the boundary line should be maintained when the obtained value is smaller than the predetermined value, and determining that the boundary line should be corrected when the obtained value is greater than the predetermined value, where K=1.8.

8. The method according to claim 6, wherein the sub-step of correcting the boundary line using the curve generating method is performed by applying the curve generating method to the adjacent protruded pixels and two pixels separated outward from the adjacent protruded pixels by 30 pixels.

9. The method according to claim 1, wherein the region separating step includes a binarization sub-step of calculating an optimal threshold value and displaying only the lean region.

10. The method according to claim 9, wherein the optimal threshold value is calculated in the binarization sub-step by:
analyzing a gray-scale level using a brightness distribution of an image in a green band;
excluding a region where the gray-scale level of the image in the green band is less than 25 and a region where the gray-scale level is greater than 150 and reducing the gray-scale level in the remaining region to a half;
calculating a probability distribution of the lean region and a probability distribution of a fat region using probability density functions of the gray-scale levels, a sum of probability density functions of the lean region, and a sum of probability density functions of the fat region;
applying a probability distribution of the lean region and a probability distribution of the fat region to $\alpha$-dimension Rényi entropy;
calculating the gray-scale level at which the sum of the Rényi entropy in the lean region and the Rényi entropy in the fat region is the maximum; and
calculating the optimal threshold value using the gray-scale level at which the sum of the Rényi entropy having three different values depending on the range of $\alpha$ is the maximum.

11. The method according to claim 1, wherein the grading region determining step includes an interactive checking sub-step of allowing a user to check the determined grading region and correcting the boundary line.

12. The method according to claim 1, wherein the boundary extracting step includes a labeling sub-step of labeling the lean region of which the boundary line would be extracted, a dilation sub-step of filling an empty space remaining in the labeled region, an erosion sub-step of eroding a part of the lean region exaggerated in the dilation sub-step, and an automatic boundary extracting sub-step of extracting the boundary line of the lean region determined up to the erosion sub-step.

13. The method according to claim 1, wherein the grading step includes at least one sub-step of a size determining sub-step of determining an area of a lean region, an intramuscular fat determining sub-step of determining a marbling state of beef, a color determining sub-step of determining lean and fat colors, and a fat thickness determining sub-step of determining a thickness of back fat.

14. The method according to claim 13, wherein the size determining sub-step includes converting the number of pixels of the grading region into an area.

15. The method according to claim 13, wherein the intramuscular fact determining sub-step includes grading the beef quality by performing a binarization process with respect to 135 using the image of the red band and by calculating tissue indexes of element difference moment, entropy, uniformity, and area ratio using four paths selected from a co-occurrence matrix as a horizontal path mask.

16. The method according to claim 13, wherein the color determining sub-step uses L*a*b* values of the International Commission on Illumination changed, which is obtained by converting average RGB values calculated from output values of an image expressed by RGB by learning using a back-propagation multi-layer neural network.

17. The method according to claim 13, wherein the thickness determining sub-step includes performing a triangular method on the grading region to detect the longest straight line in the grading region, selecting the fat part of which the thickness should be measured on the basis of the straight line, drawing a normal line perpendicular to the straight line in the selected fat region, and measuring the length of the normal line.

* * * * *